United States Patent [19]

Wiktor

[11] Patent Number: 5,653,727
[45] Date of Patent: *Aug. 5, 1997

[54] INTRAVASCULAR STENT

[75] Inventor: Dominik M. Wiktor, Cranford, N.J.

[73] Assignee: Medtronic, Inc., Minneapolis, Minn.

[*] Notice: The term of this patent shall not extend beyond the expiration date of Pat. No. 5,133,732.

[21] Appl. No.: 588,496

[22] Filed: Jan. 18, 1996

Related U.S. Application Data

[63] Continuation of Ser. No. 872,737, Apr. 22, 1992, Pat. No. 5,192,060, which is a continuation of Ser. No. 327,286, Mar. 22, 1989, Pat. No. 5,153,732, which is a continuation-in-part of Ser. No. 107,686, Oct. 19, 1987, Pat. No. 4,886,062.

[51] Int. Cl.$^6$ .................................................. A61B 17/00
[52] U.S. Cl. ............................ 606/195; 623/1; 606/191
[58] Field of Search ........................... 604/96, 104–105; 606/191–192, 194–195; 623/1, 11

[56] References Cited

U.S. PATENT DOCUMENTS

| | | |
|---|---|---|
| 3,774,596 | 11/1973 | Cook . |
| 3,868,956 | 3/1975 | Alfidi et al. . |
| 4,038,703 | 8/1977 | Bokros . |
| 4,130,904 | 12/1978 | Whalen . |
| 4,300,244 | 11/1981 | Bokros . |
| 4,319,363 | 3/1982 | Ketharanathan . |
| 4,402,307 | 9/1983 | Hanson et al. . |
| 4,503,569 | 3/1985 | Dotter . |
| 4,531,933 | 7/1985 | Norton et al. . |
| 4,553,545 | 11/1985 | Maass et al. . |
| 4,580,568 | 4/1986 | Gianturco . |
| 4,604,762 | 8/1986 | Robinson . |
| 4,619,246 | 10/1986 | Molgaard-Nielsen et al. . |
| 4,647,416 | 3/1987 | Seiler, Jr. et al. . |
| 4,649,922 | 3/1987 | Wiktor . |
| 4,655,771 | 4/1987 | Wallsten . |
| 4,665,918 | 5/1987 | Garza et al. . |
| 4,681,110 | 7/1987 | Wiktor . |
| 4,705,517 | 11/1987 | DiPisa, Jr. . |
| 4,733,665 | 3/1988 | Palmaz . |
| 4,739,762 | 4/1988 | Palmaz . |
| 4,760,849 | 8/1988 | Kropf . |
| 4,762,128 | 8/1988 | Rosenbluth . |

(List continued on next page.)

FOREIGN PATENT DOCUMENTS

| | | |
|---|---|---|
| 0183372 | 6/1986 | European Pat. Off. . |
| 837122 | 4/1952 | Germany . |
| 37-310774 | of 1962 | Japan . |
| 38-214264 | of 1963 | Japan . |

OTHER PUBLICATIONS

Charnsangavej, Chusilp, MD, et al., "Stenosis of the Vena Cava: Preliminary Assessement of Treatment with Expandable Metallic Stents" *Radiology*, Nov. 1986, pp. 295–298.

Schatz, Richard A, MD, et al., "Balloon–expandable intracoronary stents in the adult dog" *Circulation* 76(2):450–7 Aug. 1987.

Sigwart, Ulrich MD, et al. "Intravascular Stents to Prevent Occlusion and Restenosis after Transluminal Angioplasty" *New Eng J Med* 316(12):701–6. Mar 19, 1987.

(List continued on next page.)

*Primary Examiner*—Michael Buiz
*Assistant Examiner*—Nancy Mulcare
*Attorney, Agent, or Firm*—Daniel W. Latham; Harold R. Patton

[57] ABSTRACT

A medical device for use in the interior of a body lumen including a catheter and a radially expandable stent mounted on the catheter. The radially expandable stent is in the form of a hollow cylinder defined by a sequence of spaced apart wire elements with each of the wire elements extending 360 degrees around the cylinder and the wire elements having extendible, sinusoidal zig-zags lying flat with respect to the cylinder. The zig-zags are shaped in a generally longitudinal direction along the cylinder at one point and then reverse their direction so that the zig-zags may open as the wire element is expanded. The adjacent wire elements are flexibly connected together in an end-to-end fashion by helical winding.

42 Claims, 6 Drawing Sheets

U.S. PATENT DOCUMENTS

| | | |
|---|---|---|
| 4,767,418 | 8/1988 | Deininger et al. |
| 4,768,507 | 9/1988 | Fischell et al. |
| 4,776,337 | 10/1988 | Palmaz |
| 4,794,928 | 1/1989 | Kletschka |
| 4,795,458 | 1/1989 | Regan |
| 4,800,882 | 1/1989 | Gianturco |
| 4,813,925 | 3/1989 | Anderson, Jr. et al. |
| 4,830,003 | 5/1989 | Wolff et al. |
| 4,848,343 | 7/1989 | Wallsten et al. |
| 4,856,516 | 8/1989 | Hillstead |
| 4,870,966 | 10/1989 | Dellon et al. |
| 4,875,480 | 10/1989 | Imbert |
| 4,878,906 | 11/1989 | Lindemann et al. |
| 4,886,062 | 12/1989 | Wiktor |
| 4,913,141 | 4/1990 | Hillstead |
| 4,922,905 | 5/1990 | Strecker |
| 4,923,464 | 5/1990 | DiPisa, Jr. |
| 4,950,227 | 8/1990 | Savin et al. |
| 4,969,890 | 11/1990 | Sugita et al. |
| 4,986,831 | 1/1991 | King et al. |
| 4,990,155 | 2/1991 | Wilkoff |
| 4,994,071 | 2/1991 | MacGregor |
| 4,998,539 | 3/1991 | Delsanti |
| 5,002,560 | 3/1991 | Machold et al. |
| 5,007,926 | 4/1991 | Derbyshire |
| 5,015,253 | 5/1991 | MacGregor |
| 5,019,090 | 5/1991 | Pinchuk |
| 5,026,377 | 6/1991 | Burton et al. |
| 5,034,001 | 7/1991 | Garrison et al. |
| 5,037,377 | 8/1991 | Alonso |
| 5,037,427 | 8/1991 | Harada et al. |
| 5,059,211 | 10/1991 | Stack et al. |
| 5,062,829 | 11/1991 | Pryor et al. |
| 5,064,435 | 11/1991 | Porter |
| 5,071,407 | 12/1991 | Termin et al. |
| 5,078,726 | 1/1992 | Kreamer |
| 5,078,736 | 1/1992 | Behl |
| 5,084,065 | 1/1992 | Weldon et al. |
| 5,089,005 | 2/1992 | Harada |
| 5,089,006 | 2/1992 | Stiles |
| 5,108,416 | 4/1992 | Ryan et al. |
| 5,108,417 | 4/1992 | Sawyer |
| 5,122,154 | 6/1992 | Rhodes |
| 5,123,917 | 6/1992 | Lee |
| 5,133,732 | 7/1992 | Wiktor |

OTHER PUBLICATIONS

Rosch, Josef, MD "Experiemental Intrahepatic Portacaval Anastomosis: Use of Expandable Gianturco Stents" *Radiology* vol. 162 No.2:481–5. Feb. 87.

Lawrence Jr., David D. MD, et al., "Percutaneous Endovascular Graft: Experiemental Evaluation" *Radiology*, vol. 163, No. 2, pp.357–360.

Early and Late Results of Intracoronary Arterial Stenting After Coronary Angioplasty in Dogs, by Roubin et al., Circulation 76, No. 4, 891–897; 1987.

Intravascular Stents to Prevent Occlusion and Restenosis After Transluminal Angioplasty, By Sigwart et al., The New England Journal of Medicine, vol. 316, Mar. 19, 1987, No. 12, pp. 701–706.

Die Intraluminal Stent–Implantation Nach Palmaz, by Palmaz, et al. Radiolage (1987) 27; 560–563.

Implantation of Balloon–Expandable Intravascular Grafts By Catheterization in Pulmonary Arteries and Systemic Vein, by Mullins et al, Circ. 77, No.1, 188–199, 1988.

Expandable Intraheptic Portacaval Shunt Stents: Early Experience in the Dog, by Palmaz et al. AJR 145: 821–825, Oct. 1985.

Angioplasty Stents May Prevent Restenosis, published in Jan. 1987 issue of Cardio, by Melissa Culverwell.

Expanding Spiral—A New Type of Prosthesis for the Palliative Treatment of Malignant Esophageal Stenosis, by E. Frimberger, Endoscopy 15 (1983) 213–214.

Balloon Expandable Intravascular Grafts by Schatz, et al., Texas Heart Institute Conference on Interventional Cardiology (Oct. 1986).

Experimental Intrahepatic Portacaval Anastomosis: Use of Expandable Gianturc Stents by Rosch et al, Radiology 1987: 162; 481–485.

Expandable Intrahepatic Portacaval Shunt Stents in Dogs With Chronic Portal Hypertension, by Palmaz, et al, AJR 147; 1251–1254, Dec. 1986.

A New Highly Flexible Balloon–Expandable Endovascular Stent: Initial Experimental Results and up to Six Months Follow–Up, Richard Stack, M.D., Duke University med. Ctr, Durham, NC, Laser One Mtg., May 11–13, 1989.

Abstract entitled: An Expandable Intravascular Stent for the Maintenance of Luminal Patency by Trent et al, presented at Fourth Annual Vascular Fellows Abstract Presentation on Apr. 28, 1988.

Expandable Intraluminal Vascular Graft: A Feasibility Study, by Palmaz, et al, Feb. 1986, Surgery pp. 199–205.

Expandable Intraluminal Graft: A Preliminary Study, by Palmaz, et al., 1985 Radiology, pp. 73–77.

Flexible Balloon–Expanded Stent for Small Vessels, by Duprat, Jr., et al., Radiology, 1987, 162:276–278.

Percutaneous Endovascular Stents; An Experimental Evaluation by Wright, et al, Radiology 1985; 156:69–72.

Abstract entitled: A New Percutaneous Balloon Expandable Stent, by White, et al, scheduled to be presented at the 61st Scientific Session of the American Heart Association in Nov. 1988.

Nonsurgical Placement of Arterial Endoprostheses: A New Technique Using Nitinol Wire by Cragg, et al, Radiology 147: 261–263, Apr. 1983.

Self–Expanding Metallic Stents for Small Vessels: An Experimental Evaluation, by Duprat, et al, Radiology 162(2): 469–72, Feb. 1987.

Normal and Stenotic Renal Arteries: Experimental Balloon Expandable Intraluminal Stenting by Palmaz, et al. Radiology 164(3): 705–8, Sep. 1987.

Technical Developments and Instsrumentation: Transluminal Expandable Nitinoil Coil Stent Grafting: Preliminary Report by Charles Dotter, M.D., et al, Radiology 147: 259–260, Apr. 1983.

Stenosis of the Vena Cava; Preliminary Assessment of Treatment with Expandable Metallic Stents, by Chamsangavej, et al. Radiology, 1986; 161; 295–298.

Radiological Follow–up of Transluminally Inserted Vascular Endoprotheses: An Experimental Study Using Expanding Spirals, by Maass et al, Radiology 1984; 152: 659–663.

Spiral Teflon Stent for Tuboplasty Involving Fimbria, by Roland et al, New York Fertility Res. Foundation, NY, Jan. 30, 1970, vol. 36, No. 3 Sep. 1970.

Atherosclerotic Rabbit Aortas; Expandable Intraluminal Grafting, by Palmaz, et al, 1986 Radiology, pp. 723–726.

****Abstract entitled: Initial Experience With a New Approach to Stenting of Peripheral and Coronary Arteries, by Sigwart, et al, Texas Heart Institute conference on interventional Cardiology (Oct. 1986) p. 59.

Abstract entitled: Maintenance of Longterm Arterial Patency By Implantation of a Metallic Prosthetic Device, by DiMassa, et al, Abstract of the 59th Scientific Sessions, AHA '86 Dallas, pp. 11–363.

Abstract entitled: Balloon Expandable Intracoronary Stents in Dogs, by Schatz, et al, Circ. vol. 74, Supp II, Oct. 1986, pp.11–458.

Abstract entitled: Histopathologic Comparison of Initial and Restenosis Lesions with Tissue From Transluminal Atherectomy by Selmon et al, Circulation, vol. 74, Supp II, Oct., 1986.

Abstract entitled: Balloon Expandable Intracoronary Stents in Dogs by Schatz et al, Circulation, vol. 74, Supp II, Oct., 1986.

Abstract entitled: Intracoronary Stenting of Canine Coronary Arteries After Percutaneous Coronary Angioplasty (PTCA) by Foubia, et al, Circulation, vol. 74, Supp II, Oct., 1986.

Abstract entitled: In Vivio Angioscopy Following Balloon Angioplasty by Hickey et al, Circulation, vol. 74, Supp II, Oct., 1986.

Expandable Intrahepatic Portacaval Shunt Stents: Early Experience in the Dog by Palmaz, et al, AJR 145:821–825, Oct. 1985.

INTRAVASCULAR STENT

CROSS REFERENCE TO RELATED APPLICATIONS

This is a continuation of application Ser. No. 07/872,737, filed on Apr. 22, 1992, U.S. Pat. No. 5,192,060, which is a continuation of Ser. No. 07/321,286, filed Mar. 22, 1989, U.S. Pat. No. 5,153,732 which is a continuation-in-part of Ser. No. 07/107,686 filed Oct. 19, 1987, now U.S. Pat. No. 4,886,062.

FIELD OF THE INVENTION

This invention relates to intravascular implants for maintaining vascular patency in humans and animals. The present invention comprises an open-ended wire formed device of basically cylinrical shape and made of a softer-then spring type metal and fitted over an inflatable element of a typical balloon type catheter such as described in U.S. Pat. No. 4,195,637 and U.S. Pat. No. 4,402,307. The wire formed device is intended to act as a permanent prosthesis stent and is implanted transluminarely. Specifically, this invention is characterized by the ability of said intravascular stent to be enlarged radially after having been introduced percutaneously, transported transluminarely and positioned at desired location. In addition, this invention relates to a method whereby a permanent prosthesis stent is implanted at the same time the angioplasty procudure is being performed. This invention is particularly useful in transluminar implantation of a stent in the field of cardiology and especially in the case of coronary angioplasty to prevent restenosis.

BACKGROUND OF THE INVENTION

In my U.S. Pat. No. 4,649,992 a device is described in combination with a catheter which is basically a compression spring retained between a partially inflated balloon and an abuttment immediately behind the balloon on the catheter shaft. The intent is to transport the spring prosthesis in this manner to the desired location and then after a successful angioplasty procedure release said spring prosthesis by totally evacuating said balloon, thus allowing said spring prosthesis to expand linearly and stay in place while the balloon catheter is withdrawn. This method is quite simple and its simplicity is very attractive; however, it has some drawbacks. One and foremost is the fact that the spring has a fixed diameter and as such is unable to fully conform to the inside wall of the vessel which at times is quite tortuous and thus could conceivably create a somewhat turbulant flow of blood, and possible thrombosis could in some cases result. Other patents, e.g. U.S. Pat. No. 4,553,545 teaches a different method where a relatively complex mechanical rotating device and co-axial cables are employed to achieve the necessary means to change the diameter of the implanted stent to a larger dimension at the point of implant. Still other patents, e.g. U.S. Pat. No. 3,868,956 describes a method wherein a temperature responsive metallic device is used and expanded after implant using external heat sources. All of the above mentioned devices present drawbacks of various magnitudes including blood coagulation and possible thrombosis and considerable complexity of procedure.

In angioplasty procedures at this time, in many cases restenosis occurs soon thereafter, which requires a secondary procedure or a surgical bypass operation. The implanted prosthesis as described herein will preclude such additional procedures and will maintain vascular patency indefinitely.

Depending on the size used, the stent according to this invention can also be efficacious in other similar applications, such as: repairs of aneurysms, support of artificial vessels or liners of vessels, initial repairs of dissections and mechanical suuport to prevent collapsing of dialated vessels. Still many other and similar applications will be satisfied by this invention without departing from the basic prewise and concept.

This stent and the method of its use particularly allows a single procedure to combine the essential angioplasty and a simultaneous implant of a permanent prosthesis designed and intended to prevent restenosis and further complications arising therefrom, also reducing the risk factor and trauma for the patient.

Another use of stents is for aortic dissection.

In the case of aortic dissection, especially a type III dissection of the descending aorta, there is no intravascular stent or prosthesis available, which is both long and flexible enough to repair a typical dissection extending the entire length from the point of origin down to the aortic bifurcation. Also, for the repair of the most difficult and most dangerous dissection, namely the type I which is that of the ascending aorta and the aortic arch, no stent is available today which could be used and be implanted intraluminarely for non-surgical repair of such a dissection. Most intravascular prosthesis and stent available today are of limited length and diameter and are especially limited in terms of flexibility and more specifically in terms of longitudinal flexibility unable to conform to tight bends and adhere to the walls of the intima and at the same time be flexible to stretch and move with each heartbeat such as experienced in the aortic arch.

Therefore, most such cases are treated medically. If surgery is necessary, it often requires the use of hypothermia and cardiopulonary bypass. Surgical procedures of this type involve high risk to the patient, a highly skilled team of cardiovascular surgeons and sophisticated equipment, because it requires the replacement of the affected region with an interpositional graft. High mortality and morbidity are associated with surgery in this region. This is especially true for the elderly and other poor candidates for a major surgery. The cost associated with such a surgical procedure is also very high.

Prior to the development of this invention, there has been no intravascular stent which would satisfy the following conditions necessary to contemplate a non-surgical repair of a dissecting aorta:

a) To be long enough to extend from the base of the aortic arch down to the aortic bifurcation.
b) To be flexible longitudinally throughout its length.
c) To be radially expandable easily, a small section at a time using common dilatation balloon or similar expanding device designed for that purpose.
d) To be radially expandable to various diameters and to conform to tortuous conditions of a diseased aorta.
e) To be non-obstructive to all branches.
f) To be clearly visible on Floroscope both during deployment and post-operatively to visibly ascertain its condition, location and efficacy.
g) To be implantable permanently, retrograde and be able to completely obliterate a false lumen of a dissection and to maintain patency of the main lumen as well, as the patency of all side branches throughout its length.

Other reference publications:
1. Self-Expanding Metalic Stents for Small Vessels *Radiology* 1987- 162.469–472.
2. Flexible Balloon-Expandable Stent for Small vessels, *Radiology*, January 1987.

3. Intravascular Stents to Prevent Occlusion and Restenosis After Transluminar Angioplasty, N. E. J. of M., Mar. 19, 1987.

4. U.S. Pat. No. 4,580,568, Percutaneous Endovascular Stent.

5. U.S. Pat. No. 4,503,569, Transluminarely Placed Expandable Graft Prosthesis, Dotter 1985.

6. U.S. Pat. No. 4,649,992, Catheter Arrangement Having a Variable Diameter Tip and Spring Prosthesis, Wiktor 1987.

7. U.S. Pat. No. 4,681,110, Catheter Arrangement and Blood Vessel Liner, Wiktor 1987.

All of the above references describe and teach various methods of providing or otherwise offering and introducing stents of different types and designs for applications similar to the one described herein in this invention.

SUMMARY OF THE INVENTION

The improvement of this invention over other similar devices such as cited in patents above, and specifically my previus invention described in U.S. Pat. No. 4,649,992, is the ability of the device of this invention to allow for and to maintain a very low profile and a small frontal area, so very important for purposes of percutaneous insertion. Thus the stent of this invention can be inserted into and be transported via a standard #8F Guiding Catheter such as USCI Cat. #006128, while using standard procedures and methods. Once on location, the stent can be expanded radially to a diameter larger than initially introduced; a ratio of =2½: 1 can easily be achieved with a wire diameter of 0.008 and initial stent diameter of 0.075. The expanded larger diameter will conform to the inside of the vessel and maintain intimate contact with the inside wall. The stent of this invention is characterized by the low memory level of the relatively easily deformable metal used for the wire.

Figure 1:
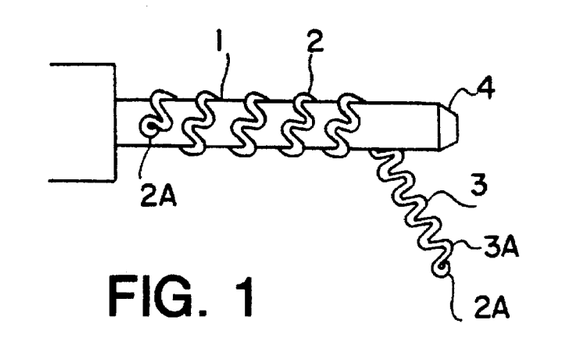
FIG. 1 is a side elevation of a preferred embodiment of a stent according to this invention being wound on a mandrel.

The configuration of stent 1, shown in FIG. 1, is such that the wire 2 is intially preformed into a two-dimensional zig-zag form 3, basically creating a flat expandable band 3a. The zig-zag pattern can vary as to its shape and tightness of the reversing bends, but for reasons of simple description a typical sinusoidal form is chosen to depict this band's construction.

Figure 5:
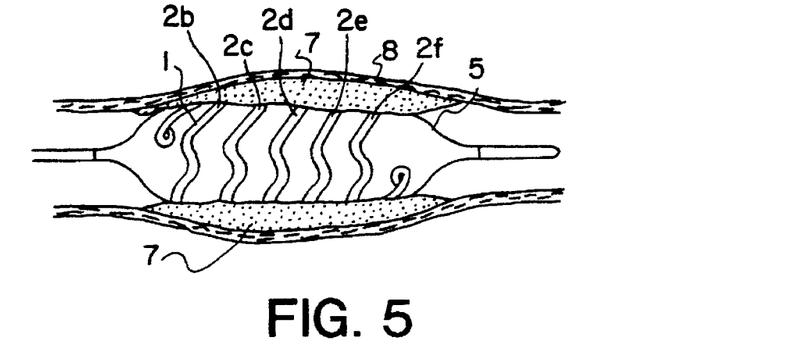
FIG. 5 is similar to FIG. 4, the balloon inflated, and the stent radially expanded, illustrating the preferred method of an angioplasty procedure coupled with a simultaneous deployment and implantation of a permanent prosthesis stent.

In order to create the stent 1, and to have it assume an initial configuration as shown in FIG. 1, also a subsequently radially expanded condition as shown in FIG. 5, a length of preformed band 3a is wrapped on a suitable mandrel 4 in a manner similar to that of winding a simple helical spring again as shown in FIG. 1. Care is taken to form the wire band 3a flat around the mandrel 4 with little or no tension to prevent premature linear expansion of band 3a.

Figure 2:
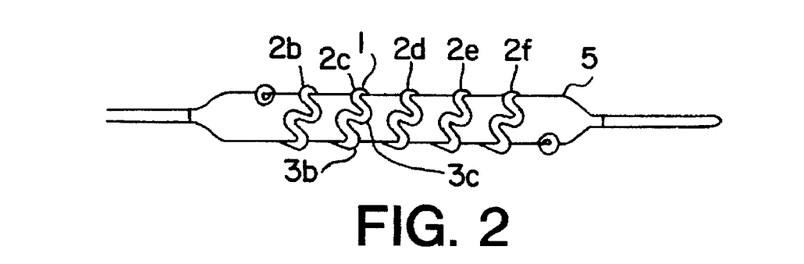
FIG. 2 is a side elevation showing an overall view of a stent prosthesis fitted over a deflated balloon.

Once the zig-zag band 3a is wound into a cylindrical shape, it is removed from the mandrel 4, and is placed over a suitable variable diameter device such as an inflatable balloon 5 typically used for angioplasty procedures as shown in FIG. 2. A suitable forming tool (not shown) is used to tighten the stent over the balloon; manual operation of squeezing the stent over the balloon is also acceptable.

Figure 4:
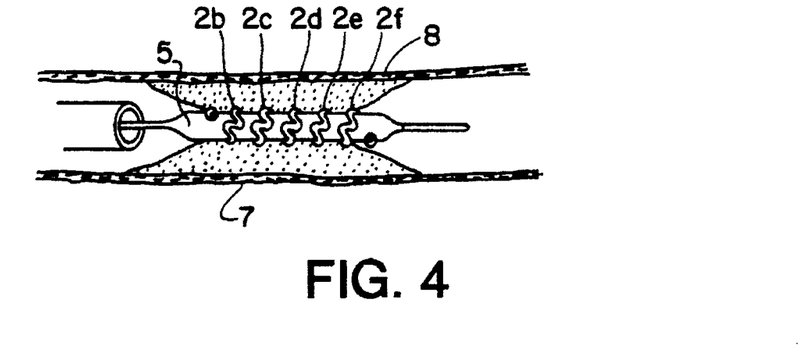
FIG. 4 is similar to FIG. 3 showing the balloon and stent assembly inside a partially occluded vessel.

Thus, according to the present invention shown in FIG. 2, a radially expandable stent 1 is in the form of a hollow cylinder defined by a sequence of spaced apart wire elements 2b–f with each of the wire elements 2b–f extending 360 degrees around the cylinder and the wire elements 2b–f having extendible, sinusoidal zig-zags 3b–c lying flat with respect to the cylinder. As shown, the zig-zags 3b–c are shaped in a generally longitudinal direction along the cylinder at one point and then reverse their direction so that the zig-zags 3b–c may open as the wire element 2c is expanded. Also as shown, the wire elements 2b–f are uniformly spaced along the cylinder and the zig-zags 3b–c are uniformly spaced around the cylinder. The adjacent wire elements 2b–f are flexibly connected together in an end-to-end fashion by means of the helical winding of the flat band 3a. As shown in FIGS. 4–5, the wire elements 2b–f can be expanded from a first diameter covering 360 degrees of the cylinder to a second, expanded diameter covering 360 degrees of the expanded cylinder.

A controlled radial expansion of the stent is accomplished by the force generated by the inflating balloon. When acted upon by the inflating balloon, the stent of this invention being characterized by the zig-zag preformed wire band 3a subsequently formed into an open-ended cylindrical shape, is by design and intent capable to expand radially.

The radial expansion in effect is achieved by controlled deformation and tension applied to the sinusoidal pattern of the preformed wire band 3a. The low memory metal used for the fabrication of the wire formed stent assures, that the radially expanded stent stays expanded thus fulfilling is preimary intent and function. Other advantages of this invention over those mentioned earlier Ref. 1 through 7, are the inherent post-expansion radial rigidity and linear flexibility, an excellent combination for an intravascular and especially intracoronary stent. In the case of intracoronary application, an overriding factor being the ability of allow for an extremely low profile and a very small frontal area so very essential for initial transluminar introduction and transportation through a standared 8F guiding catheter.

A major object of this invention is the provision of a preformed flexible wire stent which allows easy radial expansion and subsequent retention of the radially expanded shape well anchored within a vessel. Still anther object of this invention is the simplicity of its application, especially with respect to angioplasty, where one procedure accomplishes two distinct functions: In combination with the balloon it compresses the plaque, thus creating a recannalized lumen as characterized by angioplasty, and deploys and implants a permanent prosthesis within the newly created and recannalized lumen to prevent possible reclosure and restenosis thus allowing free flow of blood indefinitely. Both functions are performed simultaneously and with a single insertion of the catheter.

There is a need for a means to restrain an extra long stent from excessive stretching. This invention includes means for preventing a longitudinal overstretch of the stent, particularly during the initial introduction into the vessel where several constrictions occur. The introduction of the stretch limiting means quarantees a constant and uniform pitch of the helical wire formed coil throughout the entire length of the stent both in its non-expanded and especially in its expanded condition and still maintains full flexibility. The longitudinal stretch limiting means can take several forms including a Straight wire placed on the outside of the tubular shaped stent spotwelded to each individual coil or alternately using a simple suture thread and tying each coil to the next. Another method found acceptable is to arrange the sinusoidal wave shape pattern where one wave shape out of a series is longer and can be bent to catch the wave of the adjacent coil.

The invention includes means for restraining coils of the helix from longitudinal movement relative to each other. In other words, means are provided for restraining lengthwise stretch of the coil. To one embodiment, the means includes a single lengthwise wire attached, for example, by welding to loops of the coil. In another embodiment, the loop of the coil is hooked over an adjacent loop to restrain longitudinal movement.

DESCRIPTION OF THE PREFERRED EMBODIMENT

For purposes of better and clearer understanding of this invention, reference is made to FIGS. 1–6. The preferred embodiment of this invention is shown and described in an application for angioplasty; however, it is understood that other applications not specifically mentioned herein are ossible and no limitations in scope of this invention are intended or implied without departing from the basic principles of this invention.

FIG. 1 shows the details of construction of the prosthesis stent 1, hereafter called stent, which is basically of a hollow open-ended cylindrical shape. Stent 1 is basically a tubular shape of coiled preformed wire band typically wound on a suitable mandrel 4. The wire is made of drawn low-memory level material such as stainless steel, titanium ASTM F63–83 Grade 1 or high carat gold K 19–22. Copper alloy typically 110 when properly coated with polyester or Teflon® can also be used. Titanium and gold are biologically compatible and inert and requires no special treatment.

Figure 6:
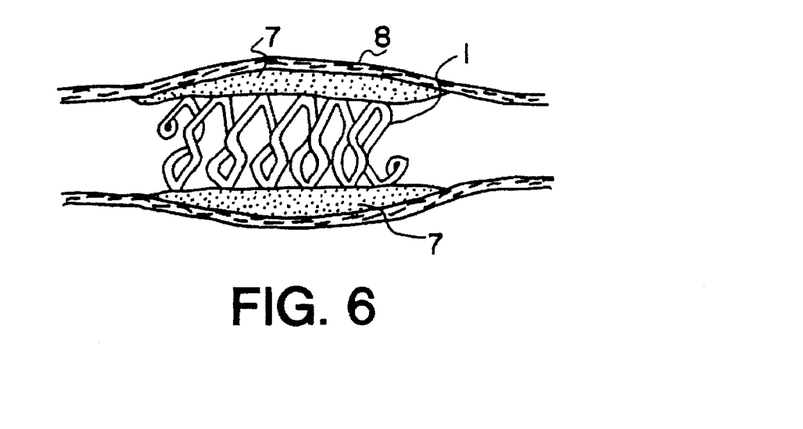
FIG. 6 is a view similar to FIG. 5 showing the prosthesis stent implanted and plaque compressed and retained after removal of the balloon.

In FIG. 2, it is shown that the stent 1 is centrally located and positioned with respect to the length of balloon 5 and that flat preformed wire band 3a turns are evenly spaced so that when stent 1 is expanded as shown in FIG. 5 and FIG. 6, stent 1 will provide even support inside vessel 8, and be able to resist external loading.

Figure 3:
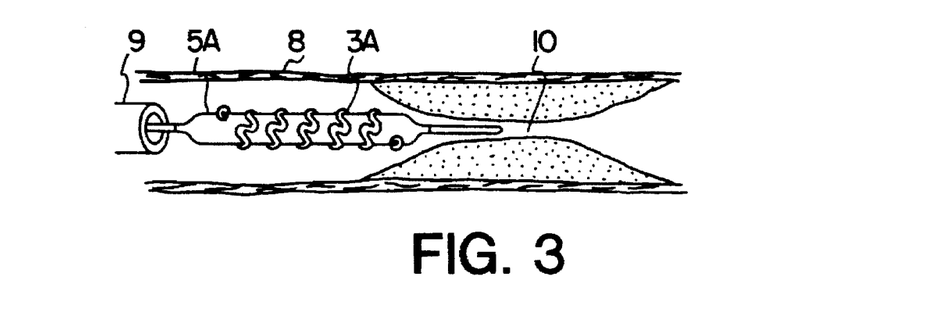
FIG. 3 shows the balloon and stent assembly advanced within a vessel, approaching a partial occlusion.

In FIG. 3, it is shown how balloon and stent assembly 5a emanate from guiding catheter 9 inside vessel 8 and is advanced towards partial occlusion 10.

In FIG. 4, it is shown how balloon and stent assembly 5a are located inside occlusion 10 within arter 8, balloon 5 still being deflated. Once positively placed within occlusion 10, balloon 5 is inflated using standard angioplasty procedures and techniques. As balloon 5 expands, so does the stent 1 as shown in FIG. 5. The expanding balloon 5 together with stent 1 compresses the plaque 7, said plaque remains compressed and stent 1 retains said plaque 7 and prevents possible reocclusion. Angioplasty procedure complted, balloon 5 is deflated and withdrawn leaving stent 1 firmly implanted within vessel 8. Previously occluded vessel 8 is now completely recannalized and patency is restored.

FIG. 6 shows stent 1 firmly implanted and imbedded in compressed plaque 7, providing both adequate support as well as a smooth lumen void of all protrusions, a very desirable feature and condition, since any protrusions are conductive to turbulant blood flow and potential formation of thrombosis.

To test the viability of this novel principle of stent construction, a polyester-coated copper wire of 0.008 diameter was preformed into a zig-zag pattern 3 as shown in FIG. 1 to form a band 3a. This band was subsequently wound into a tubular shape with ends curled into tight loops 2a to prevent sharp ends of wire 2 from perforating balloon 5. The tubular stent was placed over a 3.5 mm PTCA 20/3.5T balloon made by SciMed and fitted tightly over said balloon. The balloon and stent assembly was fed through an 8F guiding catheter into a silastic thin-wall tubing approximately 3 mm inside diameter and balloon was inflated with a standard 10 cc syringe using plain water. The expansion of the stent was observed and documented on video. Several subsequent tests of similar nature also using larger balloons typically MeadoxSurgimed A/S Cat. No. 700720 10 mm dia. and Medi. tech halloon 12 mm dia. were used with a stent made of polyester-coated copper wire 0.014"dia. All tests showed near perfect expansion and "bench-type" implantations. Further experiments showed that multiple stents can be used in tandem. In fact, a typical balloon and stent assembly can be fed right through a previously implanted and expanded stent and be implanted downstream ahead of the previously implanted stent. A distinct advantage in real life situations.

Experimental laboratory tests on animals are now being conducted. Initial results are very encouraging and promising. Both intracoronary and intraaortic stents are being investigated at this time, a complete protocol is being prepared.

Five stents recently implanted in small arteries of pigs and expanded to 3.5 mm have successfully maintained 100% patency for several weeks and as of this date continue to do so.

In sparate experiment, a previously aortic dissection has been stopped by expanding a 10 mm diameter stent within said dissection.

Figure 7:
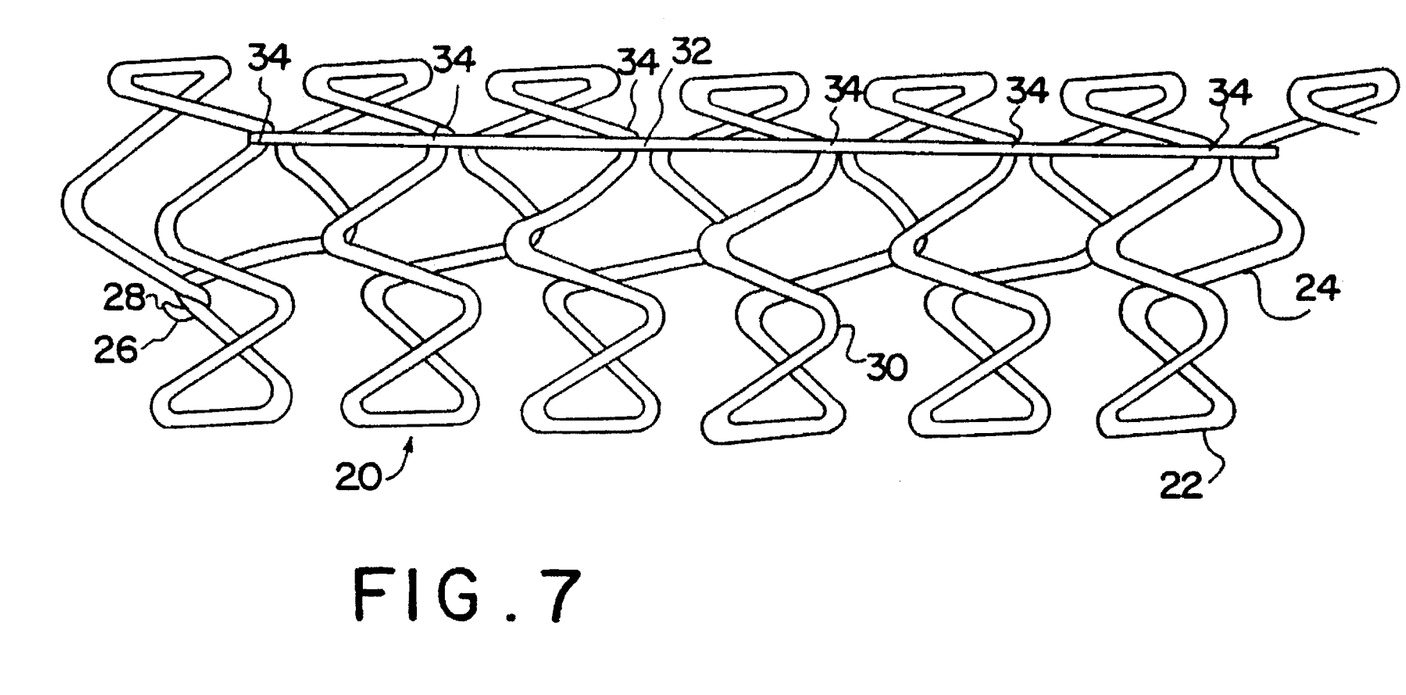
FIG. 7 shows the stent with one type of a longitudinal over-stretch limiting means.

The embodiment of the present invention involving means for preventing longitudinal overstretching is illustrated in FIG. 7. Stent 20 has a generally cylindrical body 22 formed by winding wire 24 in the cylindrical shape, as discussed above. Wire 24 has an end 26 which has a loop 28 hooked over wire 24.

Wire 24 has been formed with zig-zags or waves 30, as in the embodiments discussed above. A longitudinal wire 32 is attached, preferably by welding, to waves 30 of wire 24 at points 34.

Wire 32 prevents stent 20 from expanding along the longitudinal axis of wire 32. Radial expansion of the cylindrical body 22 is accomplished by stretching waves 24, as in the embodiments discussed above.

The structure of FIG. 7 is particularly suitable for long stents which may be more susceptible to stretching. One example is in the case of aortic dissections.

Figure 8:
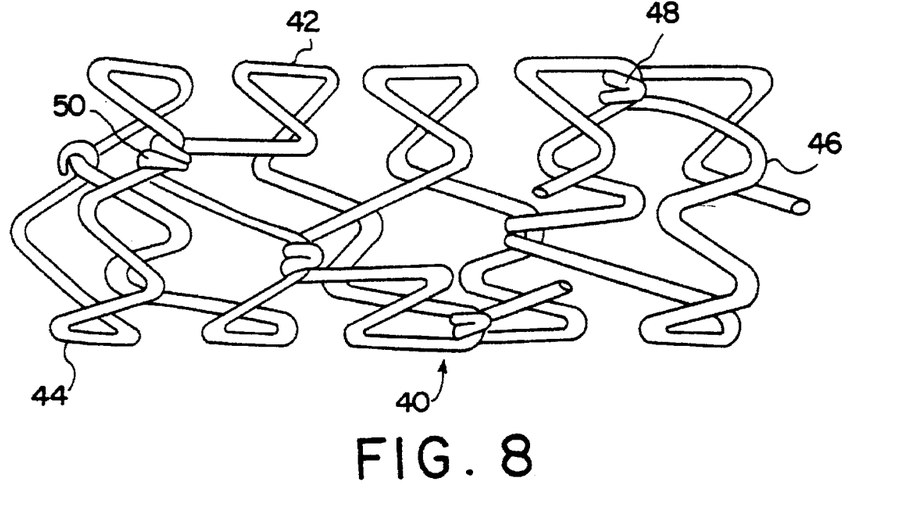
FIG. 8 shows the stent yet with another means to prevent longitudinal over-stretch.

In FIG. 8, it is illustrated an alternative embodiment of means for preventing longitudinal overstretch in a stent constructed according to the present invention. Stent 40 has a generally cylindrical body 42 formed of wire 44. Wire 44 has zig-zags or waves 46.

Certain of waves 46 are longer than others, such as waves 48. In this embodiment, one out of four of waves 46 is elongated as is wave 48.

Elongated waves 48 are bent to form a loop or hook 50. Each hook 50 is looped over a wave 46 adjacent. The engagement of hooks 50 with previous waves 48 prevents longitudinal spread of the cylindrical body 42 of stent 40.

Figure 9:
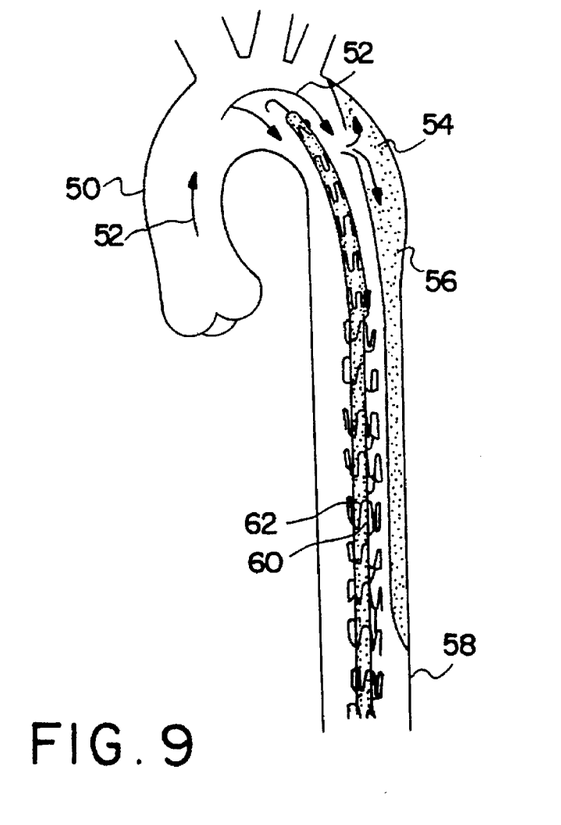
FIG. 9 shows a cross-sectional view of a typical dissection of the descending aorta including a false lumen and the expanding device and stent assembly advanced into position for first expansion.
Figure 10:
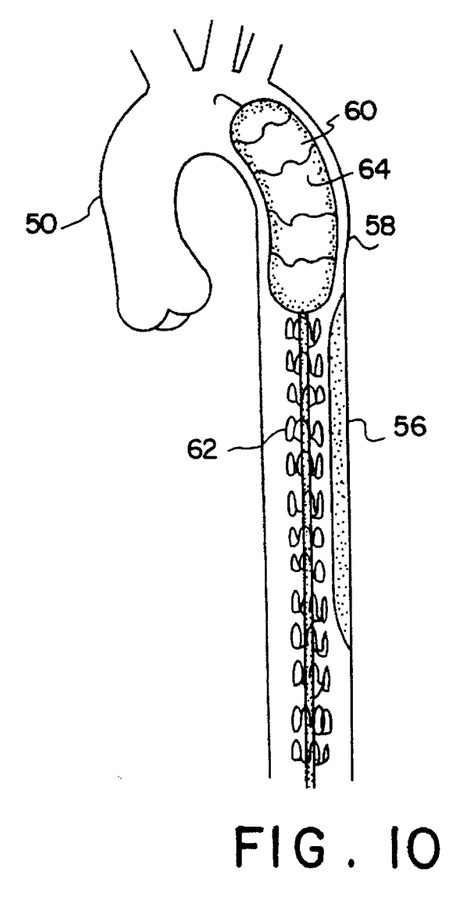
FIG. 10 shows the same cross-section of the aorta as in FIG. 9 with the flexible balloon pressurized with radio-opaque fluid and expanded.

In FIG. 9, a typical type III aortic dissection is illustrated where the aorta 50 is depicted in a cross-sectional view, and the flow of blood is shown by arrows 52. Blood partially enters the origin of dissection 54, creating a false lumen 56 by delaminating the aortic wall 58. The expanding device such as balloon 60 and stent assembly 62 is shown in a side elevation view inside the aorta 50. Balloon 60 is advanced to the point of origin of dissection 54. Balloon 60 transports extra long stent 62 and positions it within the aorta 50 for initial steps of repair. In FIG. 10, balloon 7 is shown filled with radiopaque liquid. Balloon 60 expands the stent 63 into a nearly straight wire coil 64, forcing the false lumen 56 to regress and at this point to re-laminate the aortic wall 58.

Figure 11:
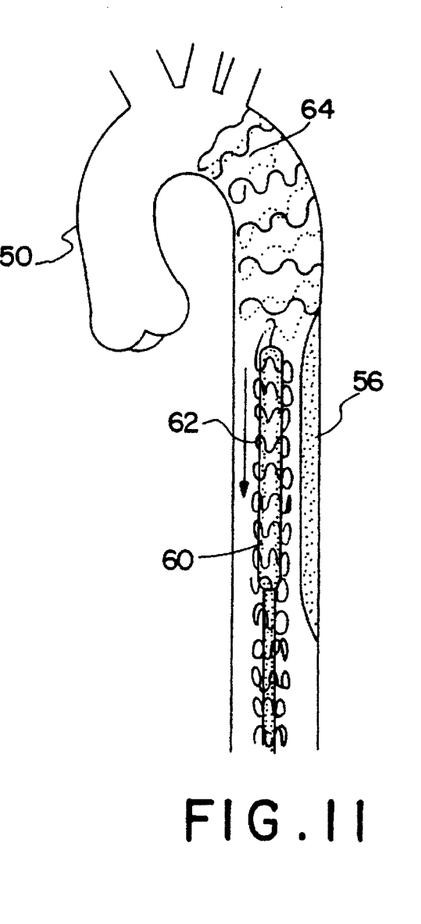
FIG. 11 shows the aorta of FIG. 10, showing the first part of the stent fully expanded, origin of dissection obliterated and expanding device repositioned for next sequential expansion.
Figure 12:
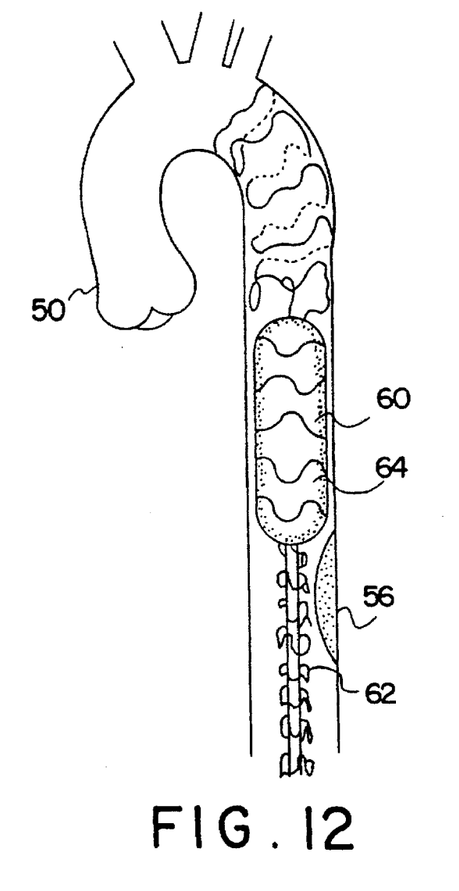
FIG. 12 depicts the next sequential expansion of the stent after FIG. 11.

FIG. 11 illustrates the expanding device 60 and stent 62 after the first stage of stent implant successfully completed, in a deflated and deactivated mode being repositioned for the next sequential procedure to expand the next portion of stent and to obliterate the next section of said false lumen 56. FIG. 12 illustrates the next portion of said false lumen 56 being obliterated by the expanding stent similar to that shown in FIG. 12.

Figure 13:
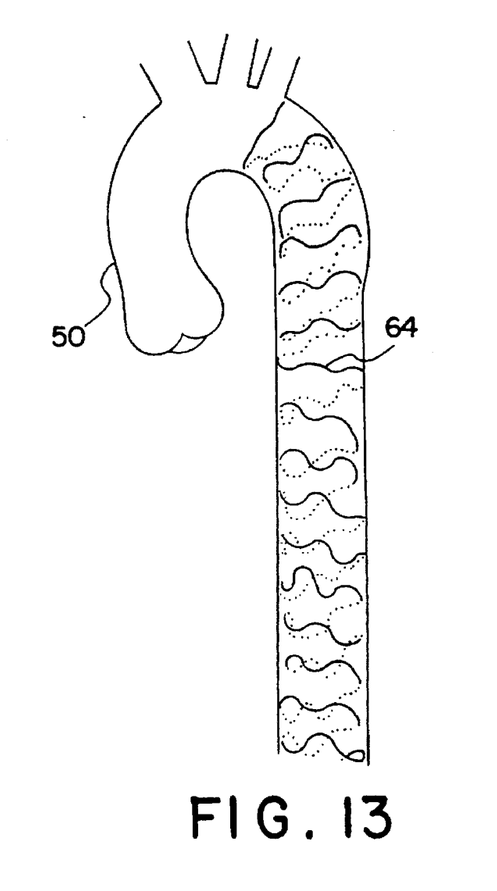
FIG. 13 shows the stent fully expanded and implanted, false lumen obliterated and type III aortic dissection repaired, and expanding device withdrawn, procedure completed.

Finally, FIG. 13 illustrates the entire length of the aorta 50 having been fitted and lined with a long flexible stent 62, said stent 62 being firmly implanted the false lumen completely obliterated and aortic dissection type III fully repaired.

For situations where a long Stent may be subjected to longitudinal stretching, either during insertion or during physiologic movement, stents constructed according to the present invention improve upon the prior art by including means for preventing longitudinal stretch. While this improvement has been disclosed in terms of particular embodiment, the prevention of longitudinal stretch by coil-type stents is a desirable goal and is facilitated by this invention.

I claim:

1. A medical device for use in the interior of a body lumen comprising:
   (a) a catheter;
   (b) a radially expandable stent mounted on the catheter, the stent comprising:
      (1) a plurality of wire elements forming a hollow cylinder, the wire elements spaced apart along the cylinder, each of the wire elements extending 360 degrees around the cylinder, and each of the wire elements having a plurality of extendible portions provided by zig-zags in the wire elements, the zig-zags made from a low memory metal, the zig-zags lying flat with respect to the cylinder which permit the wire elements to be expanded from a first diameter covering 360 degrees of the cylinder to a second, expanded diameter covering 360 degrees of the expanded cylinder; and
      (2) means for connecting adjacent wire elements together.

2. A medical device according to claim 1 wherein the zig-zags are generally sinusoidal in shape.

3. A medical device according to claim 1 wherein the second diameter is about three times the first diameter.

4. A medical device according to claim 1 wherein the wire elements are evenly spaced around the cylinder.

5. A medical device according to claim 1 wherein the zig-zags are evenly spaced around the cylinder.

6. A medical device according to claim 1 wherein the mean for connecting adjacent wire elements together includes means for providing flexibility to the stent.

7. A medical device according to claim 6 wherein the means for connecting adjacent wire elements together is an end-to-end helical winding of the wire elements.

8. A medical device according to claim 1 also comprising means on the catheter for radially expanding the stent.

9. A medical device according to claim 8 wherein the means on the catheter for radially expanding the stent is a balloon.

10. A medical device according to claim 9 wherein the stent has an end formed in a loop to prevent balloon puncture.

11. A medical device for use in the interior of a body lumen comprising:
   (a) a catheter:
   (b) a radially expandable stent mounted on the catheter, the stent comprising:
      (1) a plurality of elements forming a hollow cylinder, the elements arranged sequentially along the cylinder, each of the elements extending around the cylinder, and each of the elements having zig-zags therein, the zig-zags made from a low memory metal, the zig-zags being generally sinusoidal in shape with the zig-zags taking a generally longitudinal direction along the cylinder and then reversing their direction and lying flat with respect to the cylinder such that the zig-zags open as the stent is expanded from a first diameter to a second, expanded diameter; and
      (2) means for connecting adjacent elements together.

12. A medical device according to claim 11 wherein the elements extend 360 degrees around the cylinder.

13. A medical device according to claim 11 wherein the elements are wire elements.

14. A medical device according to claim 11 wherein the second diameter is about three times the first diameter.

15. A medical device according to claim 11 wherein the elements are evenly spaced along the cylinder.

16. A medical device according to claim 11 wherein the zig-zags are evenly spaced around the cylinder.

17. A medical device according to claim 11 wherein the means for connecting adjacent elements together includes means for providing flexibility to the stent.

18. A medical device according to claim 17 wherein the means for connecting adjacent elements together is an end-to-end helical winding of the elements.

19. A medical device according to claim 11 also comprising means on the catheter for radially expanding the stent.

20. A medical device according to claim 19 wherein the means on the catheter for radially expanding the stent is a balloon.

21. A medical device according to claim 20 wherein the stent has an end formed in a loop to prevent balloon puncture.

22. A medical device for use in the interior of a body lumen comprising:

(a) a catheter:

(b) a radially expandable stent mounted on the catheter, the stent comprising:

(1) a plurality of elements forming o hollow cylinder, the elements spaced apart along the length of the cylinder, each of the elements extending 360 degrees around the cylinder, and each of the elements having a plurality of extendible portions made from a low memory material lying flat with respect to the cylinder which permit the elements to deform and be expanded from a first diameter covering 360 degrees of the cylinder to a second, expanded diameter covering 360 degrees of the expanded cylinder; and (2) means for connecting adjacent elements together including means for providing flexibility to the stent.

23. A medical device according to claim 22 wherein the plurality of extendible portions are provided by zig-zags in the element.

24. A medical device according to claim 23 wherein the zig-zags are generally sinusoidal in shape.

25. A medical device according to claim 23 wherein the elements are wire elements.

26. A medical device according to claim 22 wherein the second diameter is about three times the first diameter.

27. A medical device according to claim 22 wherein the elements are evenly spaced along the cylinder.

28. A medical device according to claim 22 wherein the zig-zags are evenly spaced around the cylinder.

29. A medical device according to claim 22 wherein the means for connecting adjacent elements together is an end-to-end helical winding of the elements.

30. A medical device according to claim 22 also comprising means on the catheter for radially expanding the stent.

31. A medical device according to claim 30 wherein the means on the catheter for radially expanding the stent is a balloon.

32. A medical device according to claim 31 wherein the stent has an end formed in a loop to prevent balloon puncture.

33. A medical device for use in the interior of a body lumen comprising:

(a) a catheter:

(b) a radially expandable stent mounted on the catheter, the stent comprising:

(1) a plurality of elements forming a hollow cylinder, the elements spaced apart along the length of the cylinder, each of the elements extending 360 degrees around the cylinder, and each of the elements having a plurality of extendible portions lying flat with respect to the cylinder which permit the elements to be expanded from a first diameter covering 360 degrees of the cylinder to a second, expanded diameter covering 360 degrees of the expanded cylinder; and (2) means for flexible, helical connection of adjacent elements.

34. A medical device according to claim 33 wherein the plurality of extendible portions are provided by zig-zags in the element.

35. A medical device according to claim 34 wherein the zig-zags are generally sinusoidal in shape.

36. A medical device according to claim 33 wherein the elements are wire elements.

37. A medical device according to claim 33 wherein the second diameter is about three times the first diameter.

38. A medical device according to claim 33 wherein the elements are evenly spaced along the cylinder.

39. A medical device according to claim 34 wherein the zig-zags are evenly spaced around the cylinder.

40. A medical device according to claim 33 also comprising means on the catheter for radially expanding the stent.

41. A medical device according to claim 40 wherein the means on the catheter for radially expanding the stent is a balloon.

42. A medical device according to claim 41 wherein the stent has an end formed in a loop to prevent balloon puncture.

* * * * *